United States Patent
White et al.

(10) Patent No.: US 8,828,022 B2
(45) Date of Patent: Sep. 9, 2014

(54) HYBRID STONE RETRIEVAL DEVICE

(75) Inventors: Curtis White, Spencer, IN (US); Brad Elliott, Bloomington, IN (US); James S. Bates, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1281 days.

(21) Appl. No.: 11/030,044

(22) Filed: Jan. 7, 2005

(65) Prior Publication Data

US 2005/0216031 A1    Sep. 29, 2005

Related U.S. Application Data

(63) Continuation of application No. 10/057,535, filed on Jan. 24, 2002, now Pat. No. 6,872,211, which is a continuation of application No. 09/559,385, filed on Apr. 26, 2000, now Pat. No. 6,350,266, which is a continuation-in-part of application No. 09/369,226, filed on Aug. 6, 1999, now Pat. No. 6,348,056, and a continuation-in-part of application No. 08/968,906, filed on Nov. 6, 1997, now Pat. No. 6,168,603, which is a continuation of application No. 08/822,207, filed on Mar. 20, 1997, now abandoned, which is a continuation of application No. 08/382,778, filed on Feb. 2, 1995, now abandoned.

(51) Int. Cl.
*A61B 17/221* (2006.01)
*A61B 17/22* (2006.01)
*A61B 17/3205* (2006.01)
*A61B 17/00* (2006.01)

(52) U.S. Cl.
CPC ......... *A61B 17/221* (2013.01); *A61B 17/32056* (2013.01); *A61B 2017/0046* (2013.01); *A61B 17/22031* (2013.01); *A61B 2017/2212* (2013.01); *A61B 2017/2215* (2013.01); *A61B 2017/22072* (2013.01)
USPC ............ 606/114; 606/113; 606/127; 606/200

(58) Field of Classification Search
USPC ................. 606/200, 106, 113–114, 110, 127; 604/22
See application file for complete search history.

(56) References Cited

U.S. PATENT DOCUMENTS

| | | |
|---|---|---|
| 1,677,671 A | 7/1928 | Councill |
| 2,556,783 A | 6/1951 | Wallace |
| 2,943,626 A | 7/1960 | Dormia |
| 3,008,467 A | 11/1961 | Morris |
| 3,108,593 A | 10/1963 | Glassman |

(Continued)

FOREIGN PATENT DOCUMENTS

| | | |
|---|---|---|
| DE | 2 804 058 | 8/1978 |
| DE | 3 633 527 | 4/1988 |

(Continued)

OTHER PUBLICATIONS

English Translation of JP 2001252280 Kidooka et al.*

(Continued)

*Primary Examiner* — Darwin Erezo
*Assistant Examiner* — Diane Yabut
(74) *Attorney, Agent, or Firm* — Bookoff McAndrews, PLLC

(57) ABSTRACT

Baskets with multiple portions and multiple deployed configurations allow the capture and release of material within the body.

38 Claims, 15 Drawing Sheets

(56) References Cited

U.S. PATENT DOCUMENTS

| | | | |
|---|---|---|---|
| 3,137,298 A | 6/1964 | Glassman | |
| 3,472,230 A | 10/1969 | Fogarty | |
| 3,791,387 A | 2/1974 | Itoh | |
| 3,922,378 A | 11/1975 | Kline | |
| 4,046,149 A | 9/1977 | Komiya | |
| 4,046,150 A | 9/1977 | Schwartz et al. | |
| 4,198,960 A | 4/1980 | Utsugi | |
| 4,299,225 A | 11/1981 | Glassman | |
| 4,347,846 A | 9/1982 | Dormia | |
| 4,489,722 A | 12/1984 | Ferraro et al. | |
| 4,557,255 A | 12/1985 | Goodman | |
| 4,590,938 A | 5/1986 | Segura et al. | |
| 4,611,594 A | 9/1986 | Grayhack et al. | |
| 4,612,931 A | 9/1986 | Dormia | |
| 4,625,726 A | 12/1986 | Duthoy | |
| 4,633,871 A | 1/1987 | Shinozuka | |
| 4,655,219 A * | 4/1987 | Petruzzi | 606/206 |
| 4,741,335 A | 5/1988 | Okada | |
| 4,785,807 A | 11/1988 | Blanch | |
| 4,790,812 A | 12/1988 | Hawkins, Jr. et al. | |
| 4,807,626 A | 2/1989 | McGirr | |
| 4,816,339 A | 3/1989 | Tu et al. | |
| 4,865,017 A | 9/1989 | Shinozuka | |
| 4,927,426 A | 5/1990 | Dretler | |
| 4,953,548 A | 9/1990 | Stoddard et al. | |
| 4,997,435 A | 3/1991 | Demeter | |
| 5,030,201 A | 7/1991 | Palestrant | |
| 5,040,531 A | 8/1991 | Coleman et al. | |
| 5,057,114 A | 10/1991 | Wittich et al. | |
| 5,059,199 A | 10/1991 | Okada et al. | |
| 5,064,428 A | 11/1991 | Cope et al. | |
| 5,074,867 A | 12/1991 | Wilk | |
| 5,103,816 A | 4/1992 | Kirschbaum et al. | |
| 5,147,371 A | 9/1992 | Washington et al. | |
| 5,176,688 A | 1/1993 | Narayan et al. | |
| 5,190,542 A | 3/1993 | Nakao et al. | |
| 5,190,557 A | 3/1993 | Borodulin et al. | |
| 5,190,810 A | 3/1993 | Kirschbaum et al. | |
| 5,192,286 A | 3/1993 | Phan et al. | |
| 5,196,228 A | 3/1993 | Kirby et al. | |
| 5,201,740 A | 4/1993 | Nakao et al. | |
| 5,259,570 A | 11/1993 | Sochard | |
| 5,269,751 A | 12/1993 | Kaliman et al. | |
| 5,311,863 A | 5/1994 | Toppses et al. | |
| 5,312,418 A | 5/1994 | Bonnet | |
| 5,330,482 A | 7/1994 | Gibbs et al. | |
| 5,412,068 A | 5/1995 | Tang et al. | |
| 5,486,183 A * | 1/1996 | Middleman et al. | 606/127 |
| 5,496,330 A | 3/1996 | Bates et al. | |
| 5,520,697 A | 5/1996 | Lindenberg et al. | |
| 5,549,626 A * | 8/1996 | Miller et al. | 606/200 |
| 5,556,426 A | 9/1996 | Popadiuk et al. | |
| 5,658,296 A | 8/1997 | Bates et al. | |
| 5,667,525 A | 9/1997 | Ishibashi | |
| 5,755,790 A | 5/1998 | Chevillon et al. | |
| 5,836,968 A * | 11/1998 | Simon et al. | 606/200 |
| 5,957,932 A | 9/1999 | Bates et al. | |
| 6,077,274 A * | 6/2000 | Ouchi et al. | 606/113 |
| 6,093,196 A * | 7/2000 | Okada | 606/127 |
| 6,096,053 A | 8/2000 | Bates | |
| 6,099,534 A | 8/2000 | Bates et al. | |
| 6,168,603 B1 | 1/2001 | Leslie et al. | |
| 6,168,604 B1 * | 1/2001 | Cano | 606/114 |
| 6,187,017 B1 | 2/2001 | Gregory, Jr. | |
| 6,299,612 B1 * | 10/2001 | Ouchi | 606/47 |
| 6,302,895 B1 * | 10/2001 | Gobron et al. | 606/127 |
| 6,350,266 B1 | 2/2002 | White et al. | |
| 6,368,328 B1 * | 4/2002 | Chu et al. | 606/114 |
| 6,872,211 B2 | 3/2005 | White et al. | |
| 7,169,154 B1 * | 1/2007 | Que et al. | 606/127 |
| 2002/0019640 A1 | 2/2002 | McGuckin, Jr. | |
| 2002/0173815 A1 | 11/2002 | Hogendijk et al. | |

FOREIGN PATENT DOCUMENTS

| | | |
|---|---|---|
| DE | 4 025 799 | 2/1992 |
| FR | 2 275 187 | 6/1974 |
| FR | 2 275 187 | 1/1976 |
| JP | 53-30875 | 8/1978 |
| JP | 62-166813 U | 10/1987 |
| JP | 3-205043 | 9/1991 |
| JP | 2001-252280 | 9/2001 |
| JP | 2001252520 A * | 9/2001 |
| RU | 2 022 528 | 11/1994 |
| SU | 1 036 325 | 8/1983 |
| WO | WO 92/05828 | 4/1992 |
| WO | WO 92/16153 | 10/1992 |
| WO | WO 94/18888 | 9/1994 |
| WO | WO 95/05129 | 2/1995 |
| WO | WO 96/01591 | 1/1996 |
| WO | WO 96/23446 | 8/1996 |
| WO | WO 01/80748 A2 | 11/2001 |

OTHER PUBLICATIONS

Phan et al., "Ureteric Retrieval Net: Comparison with Stone Extraction by Dormia Baskets in an In Vitro Procine Model," *Brit. J. Urol.*, 73: 33-36, 1994.

Bagley et al., "Laser Division of Intraluminal Sutures," *Journal of Endourology*, vol. 12, No. 4 (1998) pp. 355-357.

Microvasic Boston Scientific Corporation Brochure: Stone Retrieval Products, p. 3-1, 3-2, 3-5, 3-6.

Microvasic Boston Scientific Corporation Brochure: Parachute™ Multi-Wire Stone Retrieval Devices, p. 3-13 and 3-14.

Japanese Office Action and Translation dated Jul. 16, 2010, in Application No. 2001-577851.

* cited by examiner

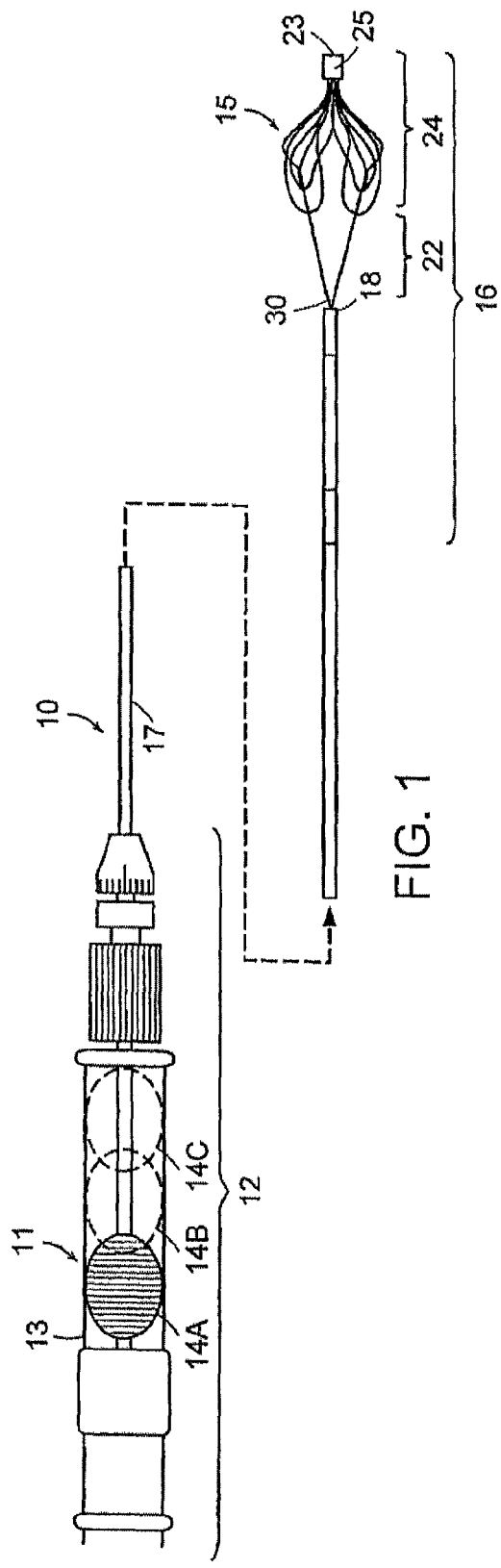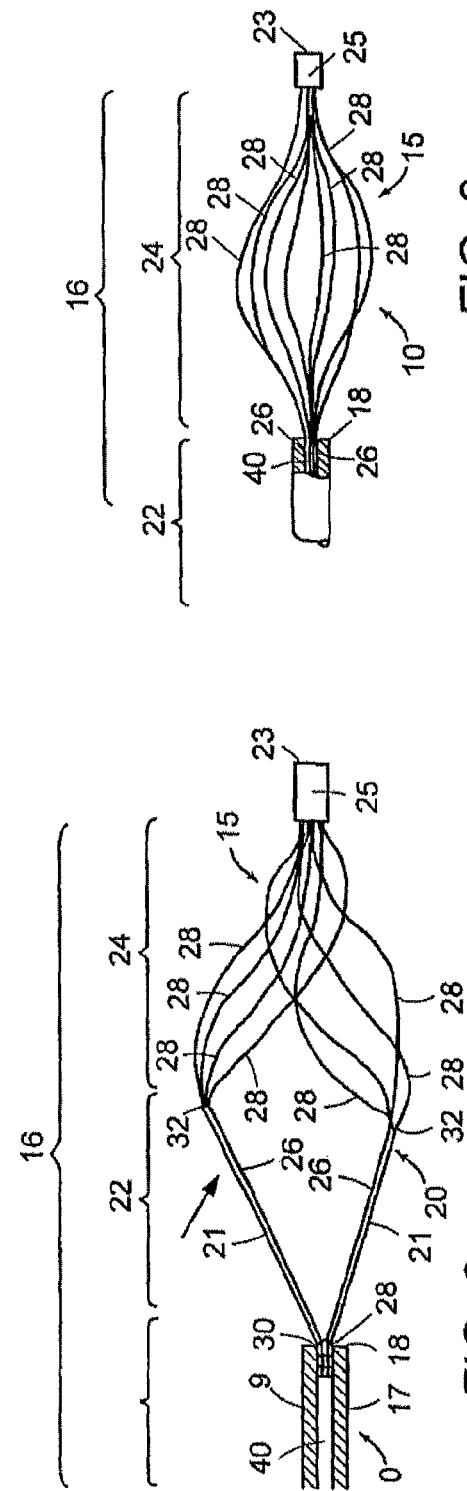

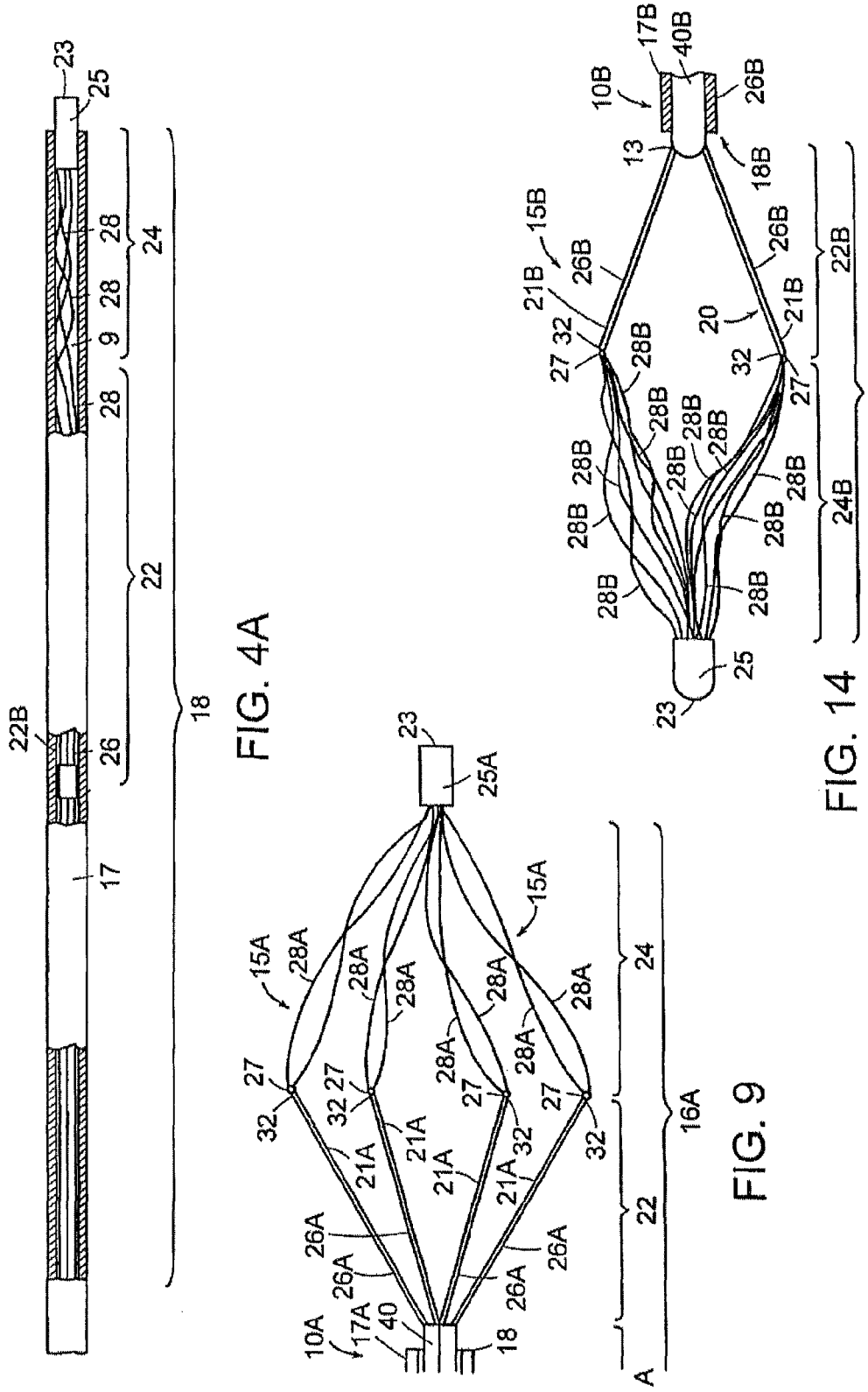

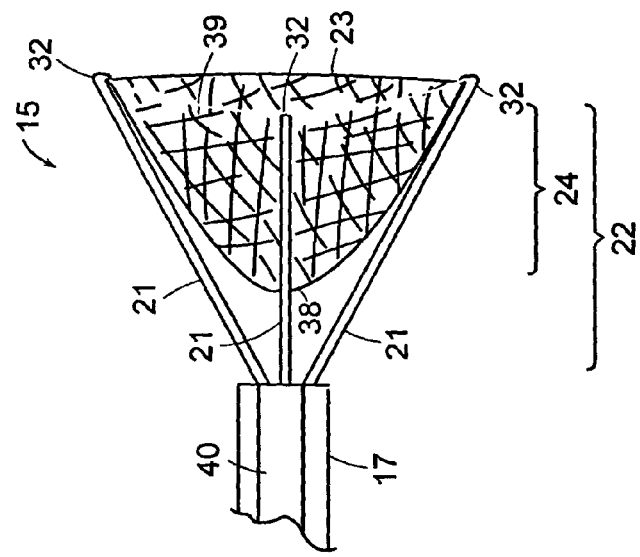
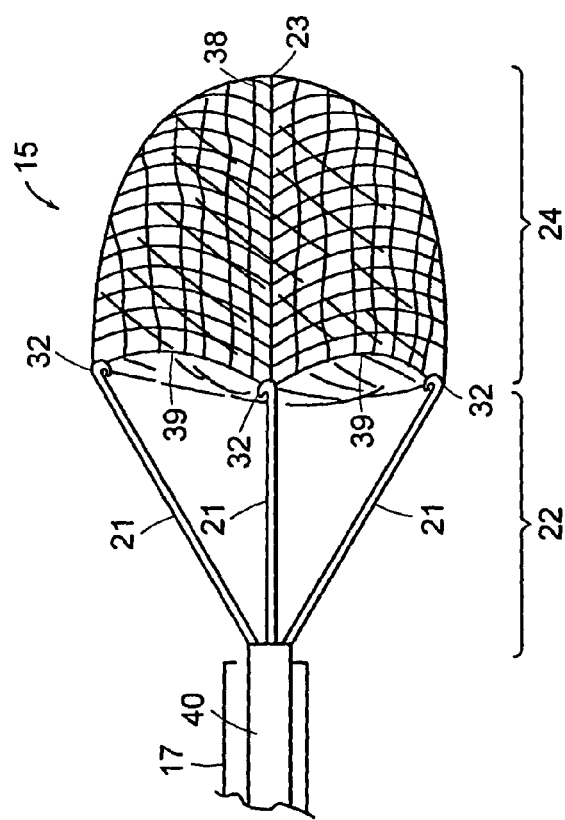
FIG. 19B
FIG. 19A

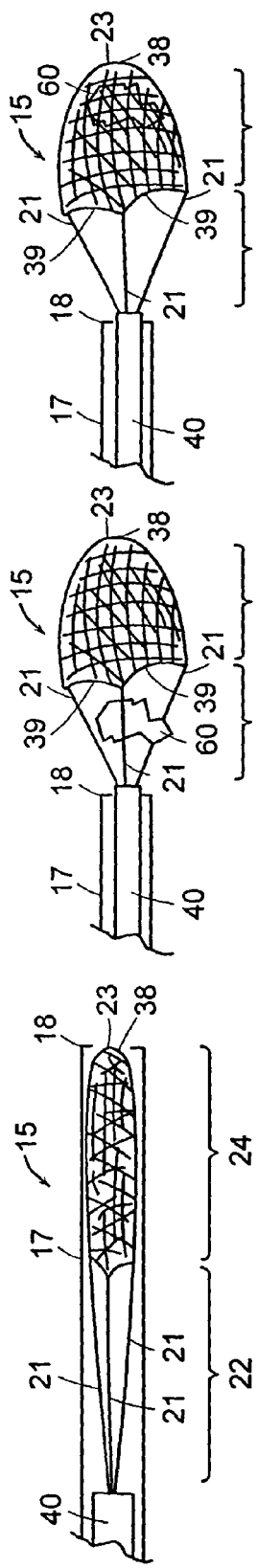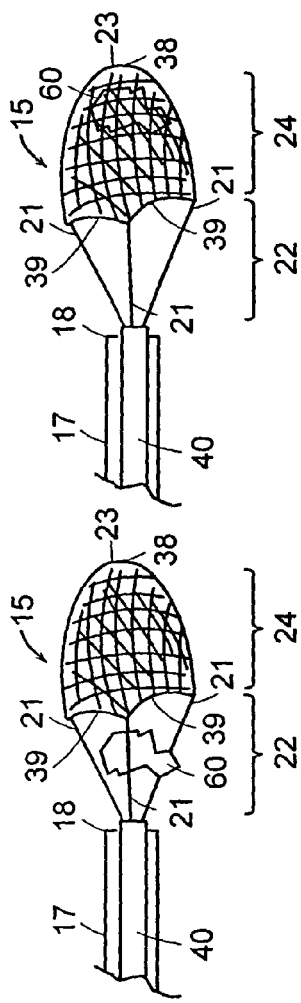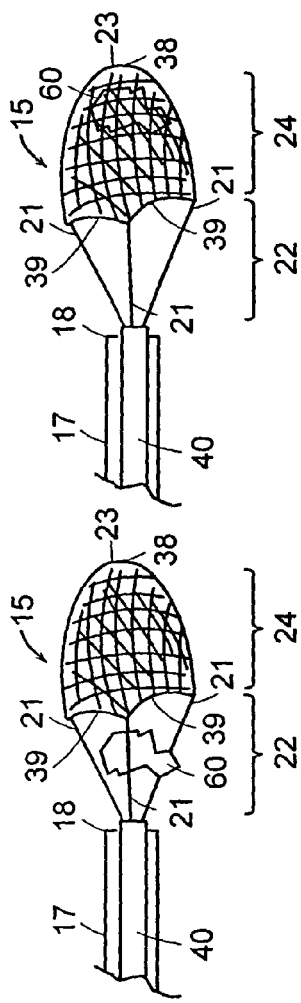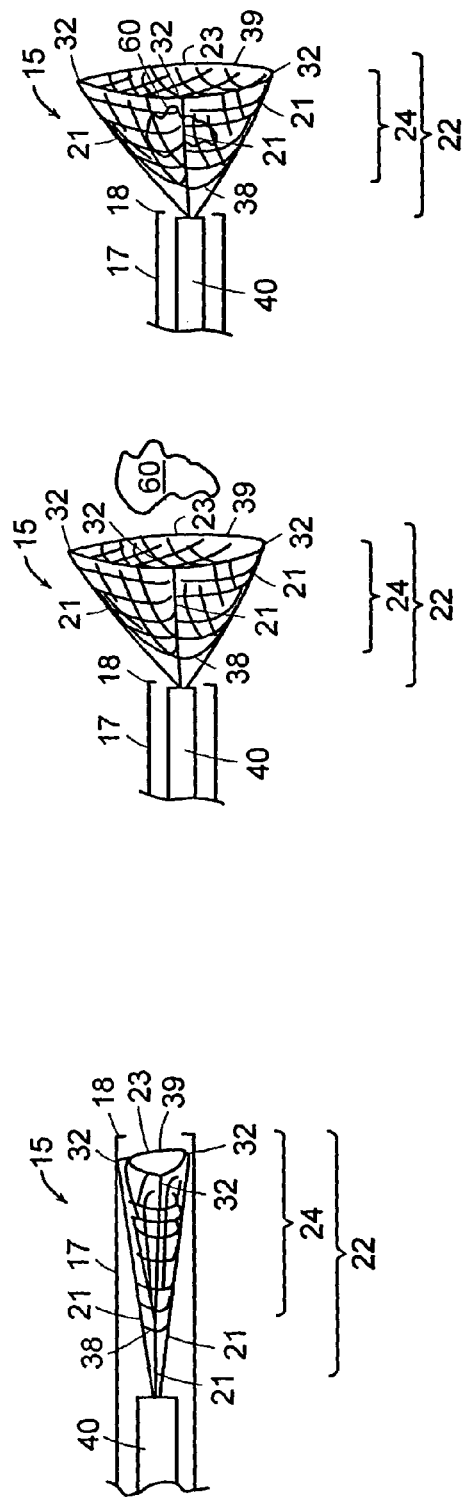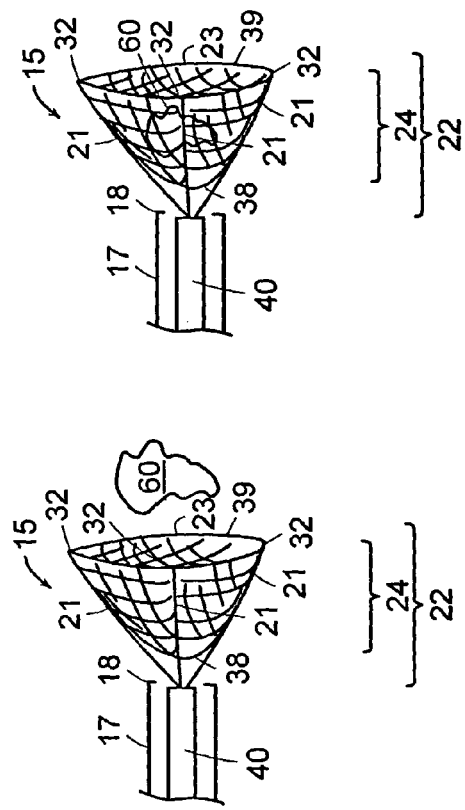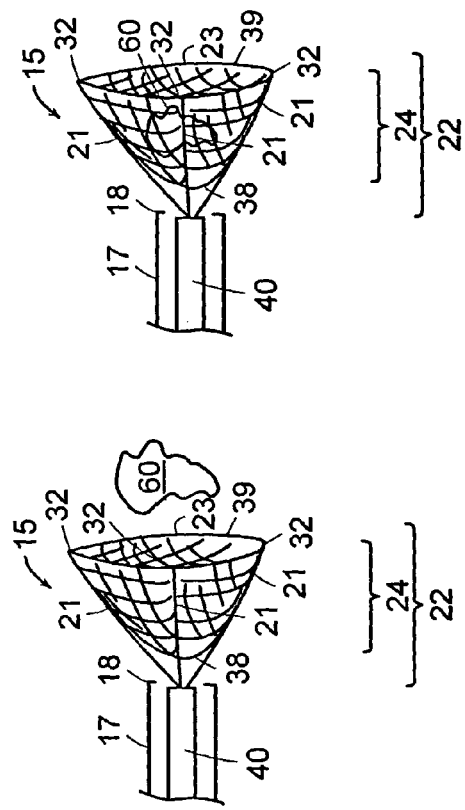

HYBRID STONE RETRIEVAL DEVICE

CROSS-REFERENCE TO RELATED APPLICATIONS

This is a continuation application of application Ser. No. 10/057,535, filed Jan. 24, 2002, now U.S. Pat. No. 6,872,211 which is a continuation of application Ser. No. 09/559,385, filed on Apr. 26, 2000, now U.S. Pat. No. 6,350,266, which is a CIP of application Ser. No. 09/369,226, filed on Aug. 6, 1999, now U.S. Pat. No. 6,348,056, and a CIP of application Ser. No. 08/968,906, filed on Nov. 6, 1997, now U.S. Pat. No. 6,168,603, which is a continuation of application Ser. No. 08/822,207, filed on Mar. 20, 1997, abandoned, which is a continuation of application Ser. No. 08/382,778, filed on Feb. 2, 1995, abandoned. The entirety of each of the above mentioned applications is incorporated herein by reference.

TECHNICAL FIELD

This invention generally relates to medical instruments such as retrieval devices for retrieving material from within a body. More particularly, the invention relates to retrieval devices for capturing and releasing stones such as urinary tract stones, gall stones, and other biological materials from a body tract.

BACKGROUND INFORMATION

Medical retrieval devices generally are used to retrieve biological and foreign material including stones from the body. Such medical retrieval devices may be used through an endoscope or a laparoscope.

One type of known medical retrieval device has a sheath and a retrieval assembly such as a basket that is movable in and out of the sheath. When the basket is within the sheath, the basket assumes a collapsed, reduced diameter profile. When the sheath is retracted relative to the basket or the basket is moved beyond the end of the sheath, the basket expands to a relatively larger diameter than when the basket is enclosed within the sheath. Generally, the contour of known baskets is round or oval and is formed by a plurality of legs.

With many known retrieval devices, materials are used in the retrieval assembly to enhance its rigidity. However, rigid materials used to enhance strength do so at the expense of flexibility. The retrieval assembly must, on the one hand, be sufficiently strong to dilate the body tract and, on the other hand, be sufficiently flexible to negotiate body tracts having small diameters, tortuous pathways and irregular lumens. Moreover, flexible retrieval assemblies can more easily capture large stones through the gaps in the legs of the retrieval assembly, than can rigid retrieval assemblies. When flexible materials are used in the retrieval assembly, however, rigidity and strength are compromised.

SUMMARY OF THE INVENTION

It is an object of the invention to provide a medical instrument, i.e., a medical retrieval device with features that permit retrieval of material within a body. The material can be biological material, such as stones, or foreign material, or any of a variety of other types of material within a body. The material can be located in a urinary or biliary tract or elsewhere in the body.

A medical instrument according to the invention is used to treat an internal organ which includes material such as a calculus or a thromboembolus. The medical instrument typically includes a proximal handle, a sheath extending from the handle and including a lumen and a distal end away from the handle, and a retrieval assembly such as a basket.

The retrieval assembly has a proximal portion and a distal portion. The proximal portion is made with a first material and the distal portion is made with a second different material.

The retrieval assembly and the sheath are moveable relative to each other to achieve a collapsed position of the retrieval assembly in which the retrieval assembly is within the lumen of the sheath and another position of the retrieval assembly in which at least a portion of the retrieval assembly extends from the distal end of the sheath. In this position, the retrieval assembly assumes a three-dimensional shape out of the lumen of the sheath.

In one embodiment, the retrieval assembly is a basket. The basket has a plurality of legs, for example, the basket has three, four, five or more legs. The legs may be preformed.

In one embodiment of the invention, the legs of the retrieval assembly feature a proximal and a distal portion. The proximal portion of the legs comprises a first material and the distal portion of the legs comprises a second material, the second material being more flexible than the first material. In this embodiment, the proximal leg portion and the distal leg portion are connected at a joint. The joint is a loop, hook, crimp, solder, weld, or any other mechanism known for connecting the ends of at least two wires or legs.

In another embodiment of the medical retrieval device of the invention, the proximal portion of the retrieval assembly is generally straight; the contour of the proximal portion being planar rather than curved. Alternatively, at least the proximal portion of the retrieval assembly is bulbous, i.e., the proximal portion is bowed out from the center of the retrieval device when the proximal portion is deployed beyond the distal end of the sheath.

Other embodiments of this invention include a sheath axially moveable relative to the retrieval assembly. In this embodiment, retraction of the sheath in a direction away from the distal end of the sheath extends the retrieval assembly from the distal end of the sheath. The portions of the retrieval assembly are thereby expanded depending on which portions are uncovered by the retracted sheath.

Some additional embodiments of the invention include an elongated guide member longitudinally positioned in the lumen of the sheath, operably attached to a proximal end of the retrieval assembly, and actuated by at least one actuating member on the handle. Reciprocal axial movement of the elongated guide member moves the retrieval assembly from its enclosed position within the sheath, in and out of the distal end of the sheath and back to its enclosed position within the sheath. As the assembly is moved in and out the sheath, the portions of the retrieval assembly shift between collapsed and opened positions.

In yet another aspect, the invention relates to a method for retrieving material from a body. The method comprises inserting a medical retrieval device with a retrieval assembly (such as the instrument described above) into a body, extending the proximal and distal portions of the retrieval assembly beyond the end of the sheath, maneuvering the retrieval assembly around the material, capturing the material within the retrieval assembly, withdrawing the proximal and distal portions of the retrieval assembly back into the sheath, and removing the medical instrument and the material captured in the retrieval assembly from the body.

BRIEF DESCRIPTION OF THE DRAWINGS

In the drawings, like reference characters generally refer to the same parts throughout the different views. Also the drawings are not necessarily to scale, emphasis instead generally being placed upon illustrating the principles of the invention.

FIG. 1 is a plan view of an embodiment of a medical retrieval device according to the invention.

FIG. 2 illustrates an embodiment of a retrieval assembly, according to the invention, extended beyond the distal end of the sheath and open.

FIG. 3. illustrates the retrieval assembly illustrated in FIG. 2 with the distal portion of the retrieval assembly extended beyond the distal end of the sheath and open.

FIG. 4A illustrates the retrieval assembly illustrated in FIG. 2 collapsed within the distal portion of the sheath.

FIG. 9 illustrates an embodiment of a retrieval assembly according to the invention.

FIG. 14 illustrates another embodiment of a retrieval assembly according to the invention.

FIG. 19A illustrates another embodiment of a retrieval assembly according to the invention.

FIG. 19B illustrates another embodiment of a retrieval assembly according to the invention.

FIG. 20A illustrates the retrieval assembly illustrated in FIG. 19A collapsed within the sheath.

FIG. 20B illustrates the retrieval assembly illustrated in FIG. 20A extended from the distal end of the sheath and open.

FIG. 20C illustrates a stone captured in the retrieval assembly illustrated in FIG. 20B.

FIG. 21A illustrates the retrieval assembly illustrated in FIG. 19B collapsed within the sheath.

FIG. 21B illustrates the retrieval assembly illustrated in FIG. 21A extended from the distal end of the sheath and open.

FIG. 21C illustrates a stone captured in the retrieval assembly illustrated in FIG. 21B.

DESCRIPTION

Figure 4B:
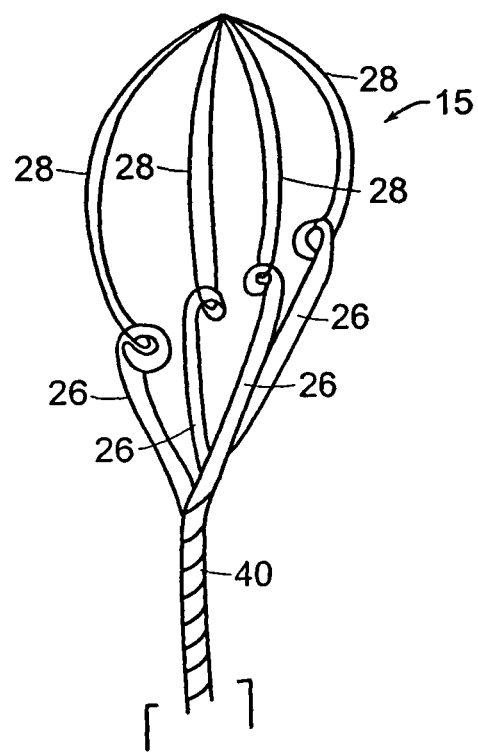
FIG. 4B illustrates an embodiment of a retrieval assembly according to the invention.

Each of the following embodiments of a medical retrieval device according to the invention have at least the following properties. The retrieval assembly of the medical retrieval device is made from a rigid material and a flexible material. The proximal portion of the retrieval assembly is made with materials that are rigid relative to the materials used in the other parts of the retrieval assembly. The materials used in the portions of the retrieval assembly other than the proximal portion enhance flexibility of those portions relative to the flexibility of the proximal portion of the retrieval assembly.

In general, in one aspect, the invention features a medical retrieval device including a handle, a sheath, and a retrieval assembly. As illustrated in FIG. 1, a medical retrieval device 1.0 includes a handle 11 at a proximal end 12 having a handle base 13 and an actuating mechanism 14, such as a slider. A physician can grasp the handle base 13 in the palm of his or her hand and manipulate the actuating mechanism 14 with his or her thumb. A retrieval assembly 15 formed in accordance with this invention is located at the distal end 16 (end furthest from operator) of the medical retrieval device 10. The retrieval assembly 15, according to the invention, may have a number of different embodiments, one of which is illustrated in FIG. 1, and will be discussed in greater detail below. A sheath 17 overlies an intermediate supporting structure, such as an elongated member 40, between the handle 11 and the retrieval assembly 15. The sheath 17 typically comprises a polyimide tube or a tube made from other materials that exhibit radial flexibility, axial stiffness, and biocompatibility.

The outside diameter of the sheath 17 can range from 1.7-8.0 French (Fr.). preferably 3.0 Fr. The retrieval assembly 15 is the type that can be collapsed within a sheath 17 for entry into the body. The handle 11, sheath 17, and retrieval assembly 15 illustrated in FIG. 1 are not shown in their correct size or proportion to each other. The size of the entire sheath is dimensioned to fit the requirements of the application of the sheath 17 in the body. For example, for urological applications, the size of the device is typically 1.7-8.0 Fr. The sheath 17 has at least one lumen 9 therein, may be made from a single material, and extends from the handle 11 to a distal sheath end 18. An elongated member 40 such as a cable, coil, shaft, guidewire or mandril wire extends within the lumen 9 from the device handle 11 to the base 30 of the retrieval assembly 15, where the elongated member 40 is attached at its distal end to the retrieval assembly 15.

The elongated member 40 is operably joined to one or more actuating mechanisms 14 at the device handle 11. Referring to FIG. 1, when the actuating mechanism 14 is located at position 14c, retrieval assembly 15 is extended beyond the distal end 18 of the sheath 17 and completely open as illustrated in FIG. 2. As the actuating mechanism 14 is moved to position 14b, the retrieval assembly 15 moves to the position depicted in FIG. 3. When the actuating mechanism 14 is moved to position 14a, the retrieval assembly is compacted by sheath 17 which covers the retrieval assembly 15 within the lumen 9 of the sheath 17 as depicted in FIG. 4A.

Alternatively, in another embodiment, the mechanism 14 can cause movement of the sheath 17 to advance the sheath 17 over the stationary retrieval assembly 15 and elongated member 40 combination, to thereby collapse the retrieval assembly 15 within the sheath 17. In this embodiment, as shown in FIG. 1, as the actuating mechanism advances from proximal position 14a to intermediate position 14b as depicted in phantom, the sheath 17 advances from the position depicted in FIG. 2 to the position shown in FIG. 3. As the actuating mechanism is advanced further to position 14c, the sheath 17 compacts and covers the retrieval assembly 15 as shown in FIG. 4A.

In general, both types of retrieval assembly/sheath movement configurations and related handle mechanisms are known, and can be seen in existing product designs available from, for example, Boston Scientific Corporation (Natick, Mass.). With the retrieval assembly 15 collapsed within the sheath 17 as shown in FIG. 4A, the sheath 17 can be inserted into the body by an operator to a site in the body where the material to be retrieved is located (e.g., a stone in the ureter). By placing the retrieval assembly 15 into its open/expanded position, as illustrated in FIG. 2, the retrieval assembly 15 dilates the body tract in which it has been placed and can be manipulated by the operator to entrap or capture material within the retrieval assembly 15.

In general, in one aspect, referring to FIG. 2, the retrieval assembly 15 is a basket formed by a plurality of legs 21. The number of legs can be as many as 2-20. In this aspect of the invention, the retrieval assembly 15 is divisible into multiple basket portions such as a proximal basket portion 22 and a distal basket portion 24. The legs 21 of the basket also have a proximal leg portion 26 and a distal leg portion 28. The proximal leg portion 26 is located within the proximal basket portion 22 and the distal leg portion 28 is located within the distal basket portion 24. The proximal end of the proximal leg portion 26 is joined to the elongated member 40 axially disposed within the lumen 9 of the sheath 17.

In general, the proximal leg portion 26 and the distal leg portion 28 of each leg 21 are made with different materials. The proximal leg portion 26 is formed with a first material that is more rigid than the second material used in the distal leg portion 28. For example, the proximal leg portion 26 is formed with stainless steel and the distal leg portion 28 is formed with Nitinol silk, nylon, other shape memory materials such as nickel-titanium, nickel-titanium-copper, and nickel-titanium-lead. Other combinations of material are also contemplated by the invention as long as the strands of the proximal leg portion 26 are more rigid than the filaments of the distal leg portion 28.

A retrieval assembly that includes a rigid proximal portion and a comparatively flexible distal portion has the advantage of providing both sufficient strength for dilating a body tract and sufficient flexibility for capturing a stone or other material within the body tract. The strands of the proximal leg portion 26 facilitate the ease by which stones or other material are captured. The gaps between the strands in the proximal basket portion 22, are comparatively wider than the gaps between the filaments in the distal basket portion 24. Moreover, the flexibility of the distal basket portion 24 permits capture of stones with diameters greater than the width of the gap between the legs 21. The filaments of the distal leg portions 28 flex to permit large stones to pass through the gaps between the legs 21 in the distal basket portion 24. After a stone is captured, the stone is trapped in the distal basket portion 24 of the retrieval assembly 15 where the gaps between the filaments of the distal leg portions 28 are comparatively narrow.

The flexible distal basket portion 24 of the retrieval assembly 15 enhances the ease by which a stone is captured when the stone is located distal to the retrieval assembly 15 or lateral to the distal basket portion 24 of the retrieval assembly 15. While the rigid proximal basket portion 22 of the retrieval assembly 15 has the strength to dilate the body tract, the flexible filaments of the distal basket portion 24 have the flexibility to flex apart to enable capture of a stone through the gaps between the filaments. The stone may enter through the distal portion of the basket via the distal end 23 of the retrieval assembly or through the side of the distal basket portion 24 of the retrieval assembly 15. Compared to rigid retrieval assemblies, the flexible distal basket portion 24 of the retrieval assembly 15 also minimizes trauma to the body tract that might result when the retrieval device is expanded in a body tract.

The filaments in the distal leg portion 28 constitute separate wires, or alternatively, the filaments are made from one wire or more than one wire, that is attached to the distal end 32 of a strand in the proximal leg portion 26 that comprises solid, twisted or braided wire. The number of filaments in the distal leg portion 28 attached to the distal end 32 of a strand in the proximal leg portion 26 is at least one, and preferably as many as 2-10.

Figure 5A:
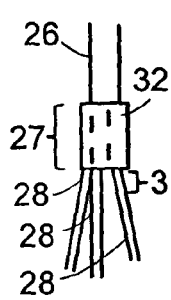
FIG. 5A illustrates a front view of an embodiment of a joint between a proximal leg portion and a distal leg portion according to the invention.
Figure 5B:
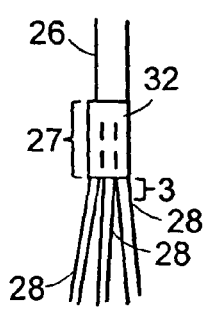
FIG. 5B illustrates a side view of the joint illustrated in FIG. 5A.
Figure 6A:
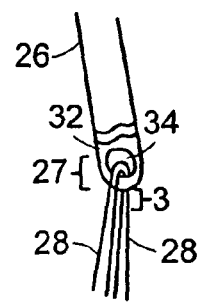
FIG. 6A illustrates a side view of an embodiment of a joint between a proximal leg portion and a distal leg portion according to the invention.
Figure 6B:
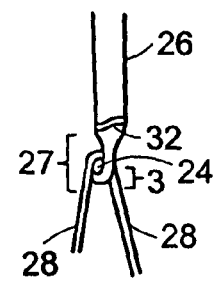
FIG. 6B illustrates a front view of the joint illustrated in FIG. 6A.
Figure 7A:
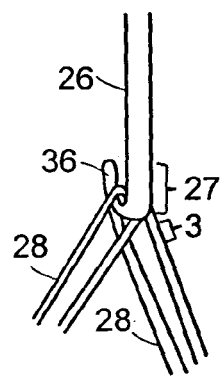
FIG. 7A illustrates a front view of an embodiment of a joint between a proximal leg portion and a distal leg portion according to the invention.
Figure 7B:
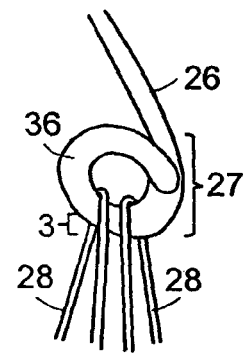
FIG. 7B illustrates a side view of the joint illustrated in FIG. 7A.
Figure 8A:
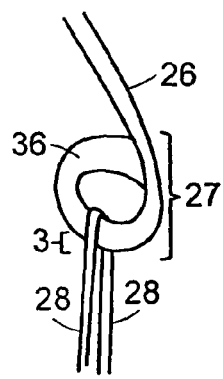
FIG. 8A illustrates a side view of a joint between a proximal leg portion and a distal leg portion according to the invention.
Figure 8B:
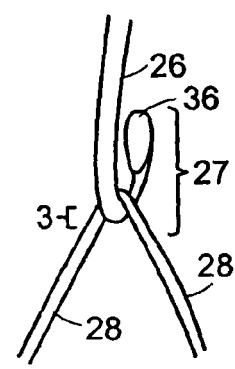
FIG. 8B illustrates a front view of the joint illustrated in FIG. 8A.

Connection of the filaments at the proximal end 33 of the distal leg portion 28 to the distal end 32 of the strands in the proximal leg portion 26 at a joint 27 is accomplished by a number of means. For example, as illustrated in FIGS. 5A and 5B, the filaments at the proximal end 33 of the distal leg portion 28 are crimped to the distal end 32 of the strands in the proximal leg portion 26 at a joint 27, or, as illustrated in FIGS. 6A and 6B, two filaments in the distal leg portion 28 are formed from a single wire that pass through a hole 34 positioned at the distal end 32 of the strand in the proximal leg portion 26. Alternatively, as illustrated in FIGS. 7A and 7B, and 8A and 8B, one or more filaments in the distal leg portion 28 passes through a partially closed loop or hook 36 positioned at the distal end 32 of a strand in the proximal leg portion 26. Other mechanisms by which the filaments at the proximal end 33 of the distal leg portion 28 are joined to the strands include solder, weld, knot, or adhesive. The number of filaments in the distal leg portion 28 that are shown in FIGS. 5A and 5B through FIGS. 8A and 8B are meant to be illustrative and are not limited to only those embodiments shown. The ratio of strands to filaments is equal to, or less than one.

In a particular embodiment, referring to FIGS. 2, 9, and 14-17, the proximal leg portion 26 of a leg 21 of the retrieval assembly 15 according to the invention, features a strand of material. The distal leg portion 28 of a leg 21 features a plurality of filaments that extend distally from each of the strands of the proximal leg portion 26 to a distal end 23 of the retrieval assembly. In one embodiment, illustrated in FIG. 2, for example, the distal ends of the filaments in the distal leg portion 28 are bundled together in an end cap 25. The cap 25 captures the distal ends of all the filaments of the distal leg portion 28 in the cap 25, by swaging or by some other means to form a distal end 23 of the basket 15.

In one embodiment, an individual strand of the proximal leg portion 26 is prestressed or preformed. Consequently, without confinement by the sheath 17, the strands in the proximal portion 22 of the retrieval assembly 15 diverge from each other as they extend distally. The filaments of the distal leg portion 28 are preformed to follow a straight or helical path from the ends of the strands in the proximal leg portion 26 to converge at the distal end 23 of the retrieval assembly to thereby define the distal leg portion 28 of the basket 15.

While FIG. 4A illustrates the strands in the proximal leg portion 26 extending essentially parallel to each other, it will be understood that the strands in the proximal leg portion 26 could be intertwined or twisted while still retaining a compact cross-section.

The strands in the proximal leg portion 26 of the proximal portion 22 of the retrieval assembly 15 could be preformed or stressed to follow a helical path between the base 30 of the retrieval assembly 15 and the distal portion 24 of the retrieval assembly 15. Additionally, as shown in FIG. 4B, the strands in the proximal leg portion 26 could vary in length to ease collapse of the retrieval assembly 15 in the sheath 17. With either of these constructions, the distal end 23 of the retrieval assembly 15 remains radially flexible and, by virtue of the sheath 17, axially stiff to facilitate placement of the retrieval device 10. At least one wire is used to make the filaments of the distal leg portion 28 in the distal portion 24 of the retrieval assembly 15. For example, as illustrated in FIG. 9, one wire is used to make two filaments of the distal leg portion 28. A section of the wire passes through joint 27 at the distal end 32 of the strand of the proximal leg portion 26 in the manner illustrated in FIGS. 6A and 6B. Both ends of the one wire are attached to the distal end cap 25. The joint 27 may take any of the forms described above, such as a hole, hook, or crimp.

Alternatively, one wire is used to make three, four, or more filaments of the distal leg portion 28. As shown in FIG. 10A, in a one wire, four filament embodiment, the one wire is passed multiple times between the joint 27, and distal end 23 of the retrieval assembly 15. It is possible to have any combination of wires to form the filaments, for example, at least one wire forming at least two filaments, and two additional wires forming two additional filaments, all four filaments extending from the distal end 32 of a single strand to form the distal leg portion 28 of a single leg 21.

Figure 10B:
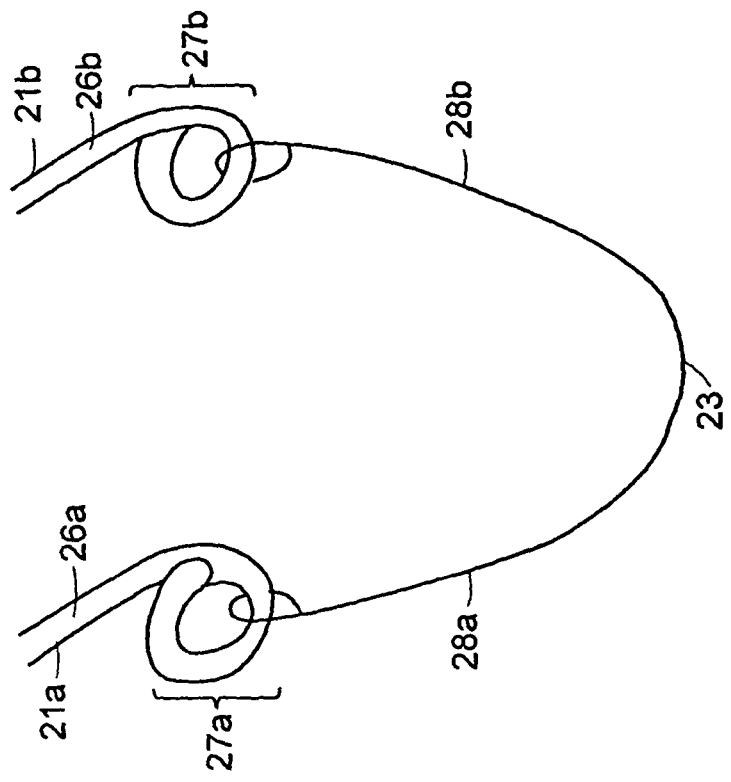
FIG. 10B illustrates an embodiment of a distal portion of two legs of a retrieval assembly according to the invention.
Figure 10A:
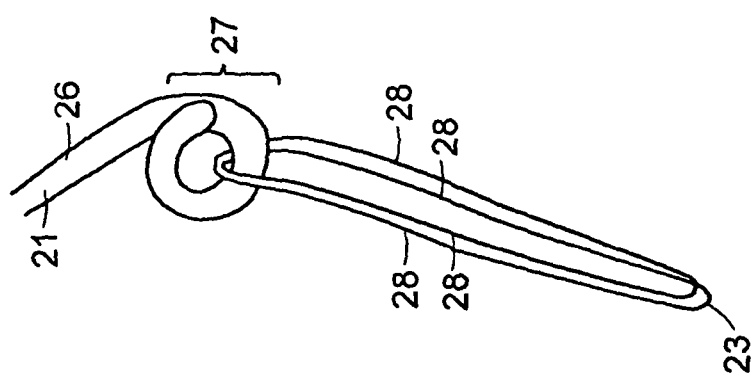
FIG. 10A illustrates an embodiment of a distal portion of a leg of a retrieval assembly according to the invention.
Figure 10C:
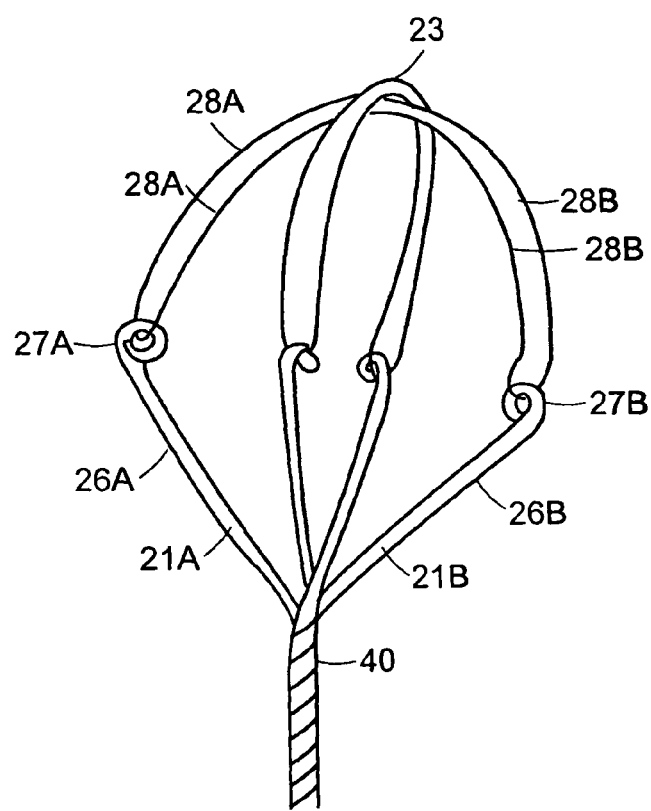
FIG. 10C illustrates an embodiment of a retrieval assembly including the legs illustrated in FIG. 10B.

In another embodiment, illustrated in FIG. 10B, the same wire may be used for filament 28a of leg 21a and for filament 28b of leg 21b. The wire passes through the joint 27a at the distal end 32 of the strand of proximal leg portion 26a, then passes distally to the distal end 23 of the retrieval assembly 15, then proximally to joint 27b at the distal end 32 of the strand of proximal leg portion 26b. In one embodiment, as illustrated in is FIG. 10C, the filaments are not attached together or to an end cap at distal end 23. In this embodiment, the retrieval assembly 15 resembles an egg whip. Alternatively, an end cap may be used to gather together the filaments at the distal end 23 of the retrieval assembly 15 illustrated in FIG. 11.

Figure 11:
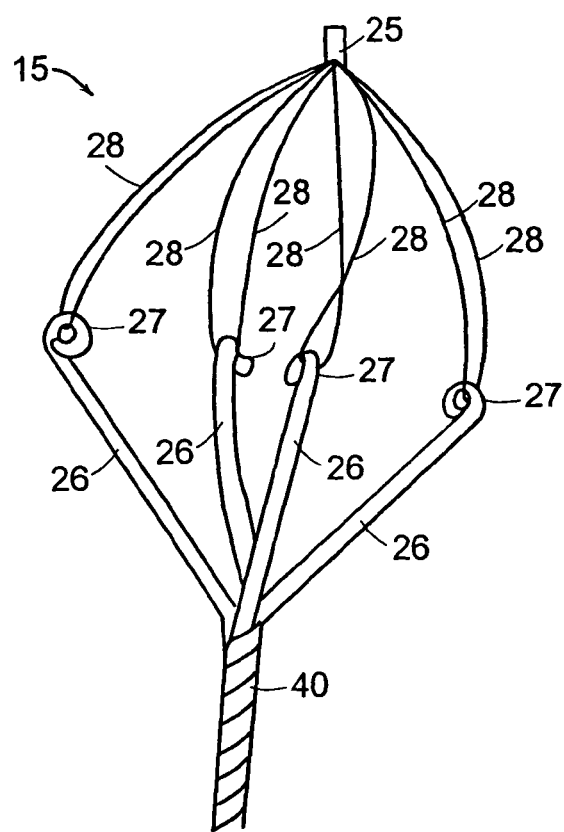
FIG. 11 illustrates an embodiment of a retrieval assembly according to the invention.

In yet another embodiment according to the invention, illustrated in FIG. 11, the strands in the proximal leg portion 26 of a retrieval assembly 15 are extensions of twisted or braided strands that form an elongated member 40 or cable. Alternatively, the proximal ends of strands in the proximal leg portion are attached to an elongated member 40 by any means such as by, for example, insertion in a short cannula, crimping, soldering, welding, swaging, or the use of an adhesive.

In a clinical application in one embodiment, an operator introduces the retrieval device 10 with its distal tip 23 of the retrieval assembly 15 in the form shown in FIG. 4A so that the sheath 17 retains the retrieval basket 15 in its compact form. When the distal tip 23 of the retrieval assembly 15 is positioned proximate calculi or any other material to be retrieved, the operator moves the actuating mechanism 14 from position 14c to the position 14A in FIG. 1. This retracts the sheath 17 and exposes the proximal portion 22 and distal portion 24 of the retrieval assembly 15. The legs 21 return to their original shape as shown in FIG. 2 thereby to dilate surrounding tissue and to provide a structure that can be manipulated to capture calculi within the confines of the retrieval assembly 15. Preferably, the distal tip 23 of the retrieval assembly 15 is positioned distally of the material to be retrieved prior to displacement of the sheath 17 so that the retrieval assembly 15 is adjacent or distally proximate to the material to ease and speed capture of the material within the retrieval assembly 15.

With the present invention, an operator can manipulate the retrieval assembly 15 so that calculi or other material move in the gap between the filaments in the distal leg portion 28 or between strands in the proximal leg portion 26. The reduced number of strands in the proximal portion 22 of the retrieval assembly 15 greatly facilitates and simplifies this task.

FIG. 9 depicts an alternative embodiment of a retrieval basket 15a and sheath 17a at a distal end 16a of the retrieval device 10a. In this particular embodiment, the retrieval is assembly 15a has four legs 21a. Each of the legs 21a has a proximal portion 26a in the form of an individual strand. A distal portion 28a of each of the legs 21a has two filaments extending from the distal end 32 of the associated one of the individual strands in the proximal leg portion 26a to a cap 25a to define a distal portion 24 of the retrieval assembly 15a. The cap 25a captures the ends of all of the filaments in the distal leg portion 28a to define the distal tip 23 of the retrieval assembly 15a. In this particular embodiment, each of the strands of the proximal leg portion 26a are angularly spaced by about 90° from adjacent strands, while the filaments of the distal leg portion 28a are helically wound and angularly spaced by about 45°.

According to the invention, the proximal 22 and distal portions 24 of the retrieval assembly 15 are collapsed within the sheath 17 in a first position. When the distal portion 24 of the retrieval assembly 15 is extended beyond the end 18 of the sheath 17, the distal portion 24 of the retrieval assembly 15 expands into a second position. When both the proximal 22 and distal portions 24 of the retrieval assembly 15 are extended beyond the distal end 18 of the sheath 17 and expanded, the retrieval assembly 15 is in a third position. Positions 1 (one) through 3 (three) of the retrieval assembly 15 are positions along a continuum from entirely collapsed to entirely expanded retrieval assembly positions.

Figure 12A:
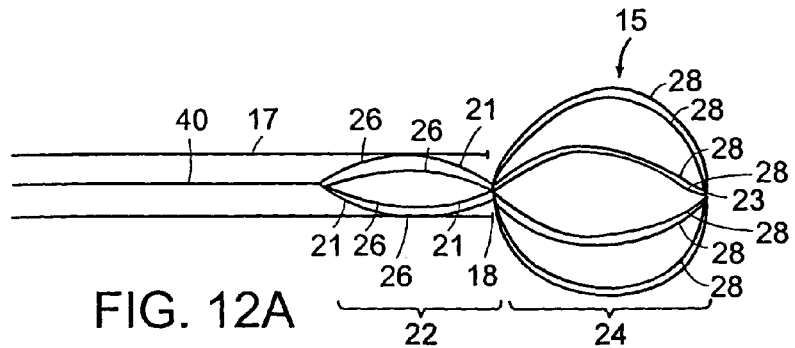
FIG. 12A illustrates an embodiment of a retrieval assembly according to the invention with the distal portion of the retrieval assembly extended from the distal end of the sheath.
Figure 12B:
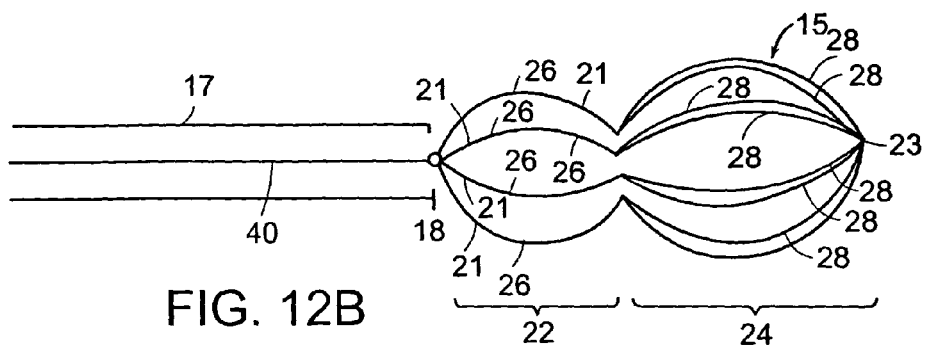
FIG. 12B illustrates the retrieval assembly in FIG. 12A with the proximal and distal portions of the retrieval assembly extended beyond the distal end of the sheath.

The contour of the retrieval assembly 15 of the invention may take a variety of shapes. Referring to FIGS. 12A and 12B, by example, an alternate embodiment of a retrieval assembly or basket 15 is shown. As shown in FIG. 12A, the basket legs 21 of the distal basket portion 24 are convex, i.e., the legs 21 are bowed out from the basket center axis. In this embodiment, as the basket moves from the first position to the second position, the distal basket portion 24 assumes a bulbous shape. When the basket 15 is extended further from the end 18 of the sheath 17, the proximal basket portion 22 extends from the end of the sheath 17 expanding as the basket 15 is moved from the second position to the third position, illustrated in FIG. 12B. The overall basket contour assumes a peanut shape.

The basket legs 21 of the basket 15 shown in FIGS. 12A and 12B may be preformed or bent before the basket 15 is assembled. The legs 21 can be bent in any manner known to one skilled in the art, for example, as detailed in U.S. Pat. No. 5,658,296, the entirety of which is incorporated by reference, herein.

Figure 13:
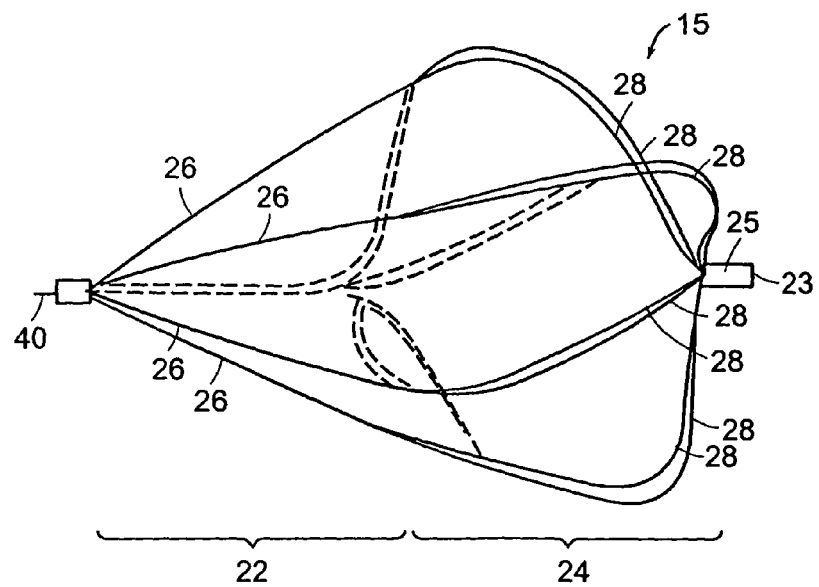
FIG. 13 illustrates a perspective view of another embodiment of the retrieval assembly according to the invention.

In another embodiment, shown in FIG. 13, the legs 21 of the proximal portion 22 of the basket 15 are substantially straight. As the basket is extended from the distal end 18 of the sheath (not shown), the distal basket portion 24 expands and the basket assumes a bulbous shape as shown in FIG. 13, second position (inner image). As the basket is extended still further from the distal end of the sheath, the proximal portion 22 of the basket expands. As shown in the third position (outer image) of FIG. 13, the overall contour of the basket 15 in the third position is cone-shaped. The diameter of the proximal basket portion 22 increases uniformly from the proximal end to the distal end of the proximal basket portion 22.

In another embodiment according to the invention, the contour of the distal basket portion 28 is helical. As illustrated in FIG. 9 for example, the distal portion 24 of the basket is comprised of a plurality of spiral-shaped filaments extending from each of the strands of the proximal leg portion 26 of each leg 21. The spiral-shaped filaments 28 may be paired. The filaments can be similar to the sets of filaments disclosed in U.S. Pat. No. 5,496,330, the entirety of U.S. Pat. No. 5,496,330 incorporated by reference, herein. As the distal basket portion 24 is extended beyond the end 18 of the sheath 17, the distal basket portion 24 expands into a substantially helical shape. The basket 20 elongates and expands as the proximal basket portion 22 is extended from the end 18 of the sheath 17 and the basket 20 assumes the third basket position illustrated in FIG. 9.

The use of multiple filaments for the distal portion 28 of a leg 21, increases the number of contact points of the retrieval assembly 15 with any entrapped calculi. In FIG. 9, for example, eight filaments in the distal basket portion 24 contact the calculi rather than four filaments. Moreover, the close equiangular spacing of adjacent filaments in a given leg also permits the wires collectively to accommodate any surface unevenness of such calculi surfaces to further increase the reliability with which the basket 15 entraps calculi.

FIG. 14 depicts the proximal and distal portions 22b and 24b of the retrieval assembly 15b at the distal end of another embodiment of a retrieval device 10b. Retraction of the sheath 17b at the distal end of the retrieval device to the illustrated position enables the proximal and distal portions 22b and 24b to form the enlarged retrieval assembly 15b extending between a cap 25b and the retrieval assembly base 30 joined to the elongated member 40b. Two legs 21 define the retrieval assembly 15b, with each of the legs comprising an individual strand 26b extending distally from the proximal end of the basket and six filaments 28b extending proximally from the distal end 23 of the basket to the distal end 32 of the associated strand 26b. The filaments 28b in this instance are prestressed to follow a helical path. The filaments 28b are joined to the strands 26b at joint 27 by any of the joints illustrated in FIGS. 5A and 5B through FIGS. 8A and 8B.

Figure 16:
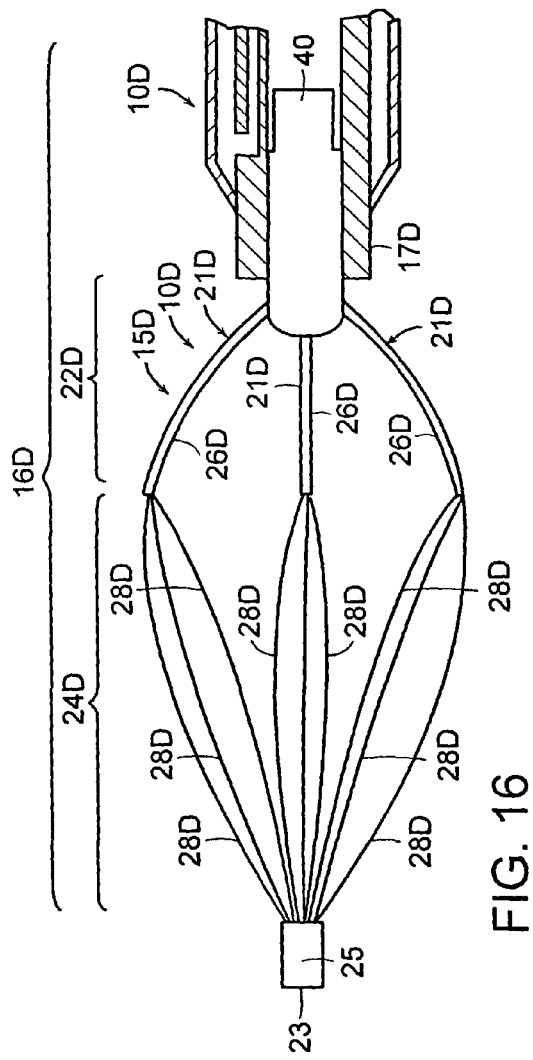
FIG. 16 illustrates another embodiment of a retrieval assembly according to the invention.
Figure 17:
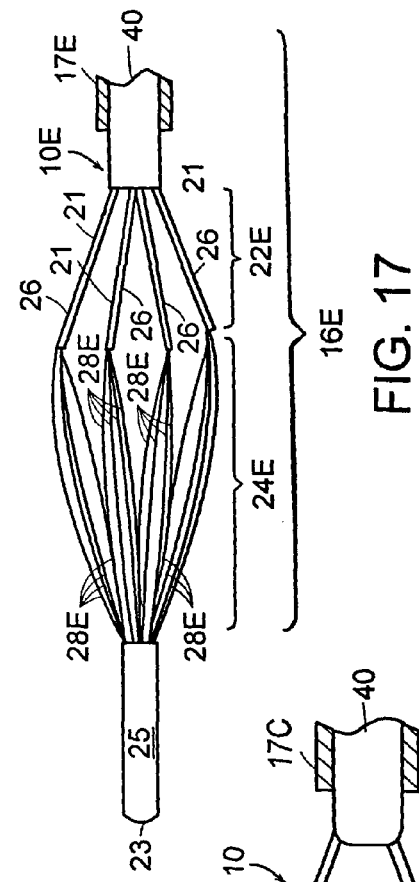
FIG. 17 illustrates another embodiment of a retrieval assembly according to the invention.
Figure 15:
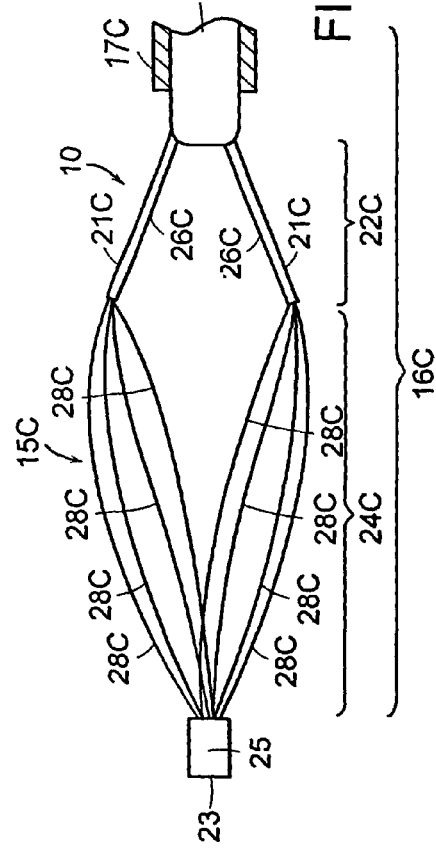
FIG. 15 illustrates another embodiment of a retrieval assembly according to the invention.

FIGS. 15-17 illustrate other retrieval device embodiments constructed in accordance with this invention. The retrieval assemblies 15c, 15d and 15e of the retrieval devices 10c, 10d and 10e comprise a plurality of legs 21 with each of the legs 21 having substantially more filaments in the distal leg portion 28 of the retrieval assembly 15 than strands in the proximal leg portion 26. For example, each of the legs 21c of the basket 15c of FIG. 15 comprises a strand in the proximal leg portion 26c and five filaments in the distal leg portion 28c, while each of the three legs 21d of the basket 15d of FIG. 16 comprise a strand in the proximal leg portion 26d and three filaments in the distal leg portion 28d. Four legs 21d define the retrieval assembly 15e of FIG. 17. Each leg 21e includes an individual strand in the proximal leg portion 26e and four filaments in the distal leg portion 28e. Although, each of the filaments of the retrieval assemblies 15c, 15d and 15e are prestressed, they are not helically wound like the filaments of the baskets 15a and 15b of FIGS. 9 and 14. For example, in FIG. 17, each of the filaments in the distal leg portion 28e between one of the strands in the proximal leg portion 26e and the cap 25e is prestressed to extend radially away from the axis of the retrieval assembly 15e and to be spaced from each of the other filaments.

The baskets 15 described in connection with FIGS. 2, 9, and 14 through 17 may also be formed by the method described in the co-pending, commonly assigned U.S. Pat. No. 5,658,296. Using the process described therein provides strands and filaments with improved strength, durability and other characteristics. In another aspect of the invention, referring to FIG. 18, a retrieval assembly features a plurality of legs 21. The legs 21 comprise a strand that is positioned in the proximal portion 22 of the retrieval assembly 15. The strands of the proximal portion 22 of the retrieval assembly are made with rigid materials, for example, stainless steel. The distal portion of the retrieval assembly features a flat distal end 23 that is positioned at the distal end 32 of the strands of the proximal leg portion 26 of the retrieval assembly 15. The distal end 23 comprises a plurality of flexible wires 29 oriented in a plane substantially perpendicular to the long axis of the retrieval device 10. At least one of the wires 29 at the distal end 23 is made with a material that is more flexible than the material comprising the strands of the proximal basket portion 22. The wires 29 comprising the distal end 23 of the retrieval assembly 15 extend from the distal end 32 of one strand of the proximal basket portion 22 to the distal end 32 of an adjacent strand or to the distal end 32 of another strand of the proximal basket portion 22. The number of legs or strands in the proximal basket portion 22 may be 3, 5, 6, 7, 8 or more and is not limited to the number of strands illustrated.

Figure 18A:
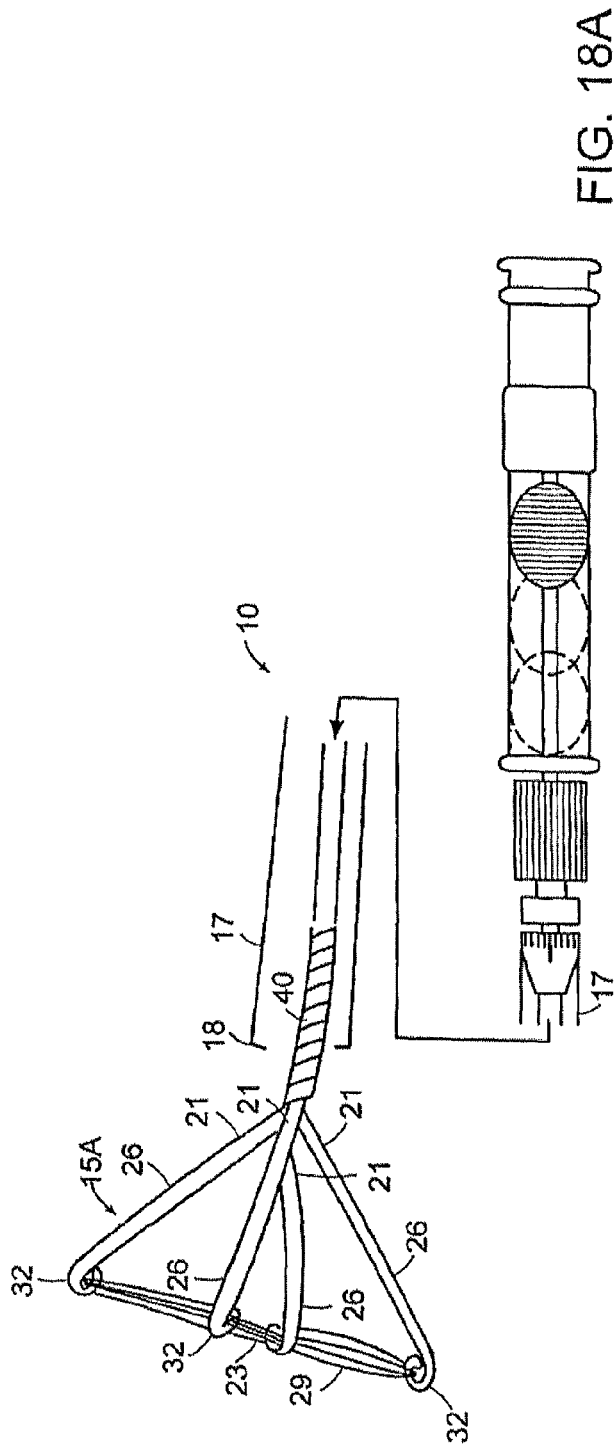
FIG. 18A illustrates another embodiment of a medical retrieval device according to the invention.
Figure 18C:
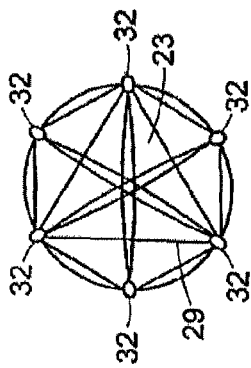
FIG. 18C illustrates an end view of another embodiment of the retrieval assembly illustrated in FIG. 18A.
Figure 18B:
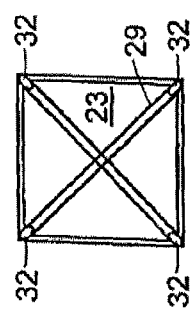
FIG. 18B illustrates an end view of an embodiment of the retrieval assembly illustrated in FIG. 18A.
Figure 18D:
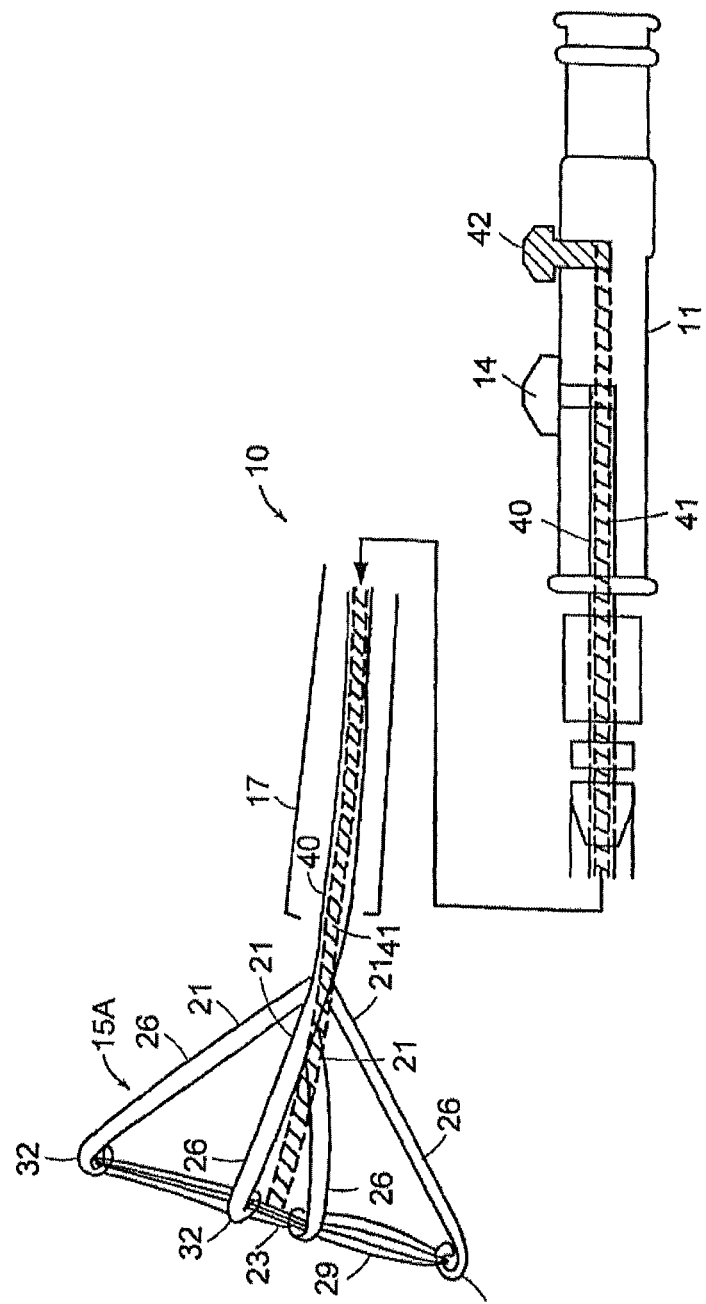
FIG. 18D illustrates another embodiment of the retrieval assembly illustrated in FIG. 18A.

As illustrated in FIGS. 18B and 18C, in one embodiment of this aspect of the invention, the distal end 23 of the retrieval assembly 15 includes at least one wire 29 that extends from the distal end 32 of one strand of the proximal portion of the retrieval assembly 22, to a distal end 32 of an adjacent strand, or, alternatively, the at least one wire 29 extends across the area defined by the distal ends 32 of the strands to the distal end 32 of another strand of the proximal leg portion. Any pattern of wires extending from the end 32 of one strand to an end 32 of another strand is contemplated by the invention. The wires 29 of the distal end 23 of the retrieval assembly 15 may form patterns other than the patterns illustrated in FIGS. 18B and 18C.

In clinical applications, the device 10 illustrated in FIG. 18A is inserted into a body tract with the retrieval assembly collapsed within the sheath 17. When the distal end 18 of the sheath passes by or is positioned adjacent to the stone or other material to be retrieved. The retrieval assembly 15 and sheath 17 are moved relative to one another to extend the retrieval assembly 15 beyond the distal end of the sheath 18 and open. The gap or distance between basket legs 21 is thereby increased. The distal end 23 of the basket 15 is maneuverable largely because of the flexible material used in making the distal end 23. The proximal portion 22 of the retrieval assembly is comparatively rigid because the proximal portion 22 is made with material more rigid than the material used in the distal end 23. Thus, the proximal portion 22 has the strength to dilate the body tract around the stone or other material and the distal basket portion 24 has the flexibility to entrap the stone or other material in the retrieval assembly 15. To capture a stone or other material, the stone passes between the gaps in the strands of the proximal portion 22 of the retrieval assembly 15 and is trapped in the confines between the strands of the proximal portion 22 of the retrieval assembly 15 and the distal end 23 of the retrieval assembly 15.

Figure 18E:
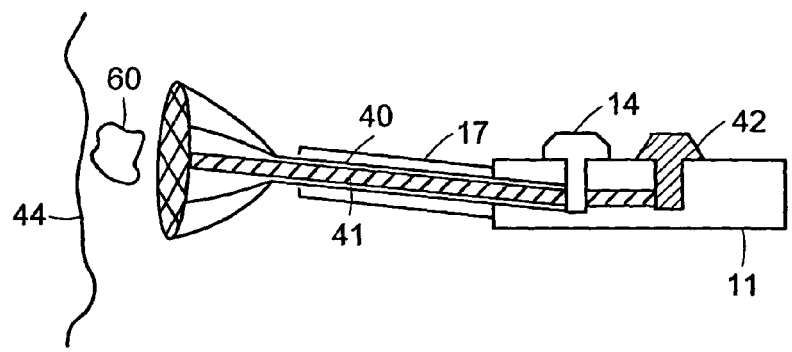
FIG. 18E illustrates the retrieval assembly illustrated in FIB 18D approaching a stone.
Figure 18F:
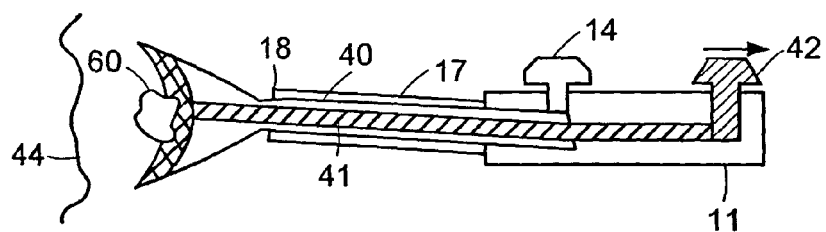
FIG. 18F illustrates the retrieval assembly illustrated in FIB 18D partially collapsed around a stone.
Figure 18G:
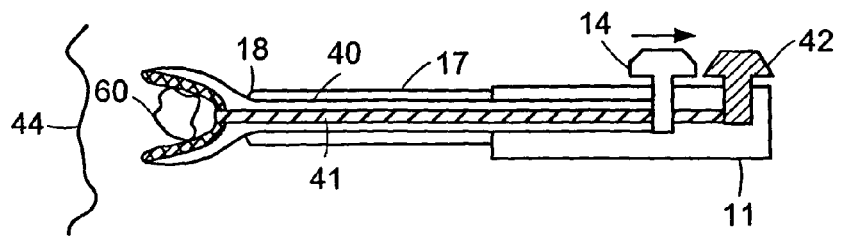
FIG. 18G illustrates the retrieval assembly illustrated in FIG. 18D collapsed around a stone and partially collapsed within the distal end of the sheath.

In an alternate embodiment of this aspect of the invention, illustrated in FIGS. 18D-18G, a second elongated guidewire 41 parallels or extends through a lumen in the first guidewire 40, and is joined at its distal end to the distal end 23 of the retrieval assembly and at its proximal end to a second actuator 42. To capture material 60 in a body tract, the retrieval assembly 15 is open and extended beyond the distal end of the sheath 17 as illustrated in FIG. 18E. A stone 60 is approached by the retrieval assembly 15 and trapped between the retrieval assembly 15 and a body tissue 44. As illustrated in FIG. 18F, the second actuator 42 is actuated proximally in the direction of the arrow to axially move the second elongated guidewire 41 proximally. The distal end 23 of the retrieval assembly 15 is thereby moved towards the distal end of the sheath 17, collapsing the retrieval assembly 15 around the stone 60. Actuator 14, illustrated in FIG. 18G, is then moved proximally in the direction of the arrow to draw the retrieval assembly 15 with the captured stone 60 partially or entirely into the distal end of the sheath 17.

In another aspect of the invention, in one embodiment, the retrieval assembly 15, illustrated in FIGS. 19A and 19B, has a proximal portion 22 and a distal portion 24. The proximal portion 22 of the retrieval assembly has a plurality of legs 21. The distal portion 24 of the retrieval assembly 15 is pocket shaped having an apex 38 and pocket edges 39 that are joined to the ends 32 of the legs 21 of the proximal basket portion 22. The proximal portion 22 of the retrieval assembly 15 is made with a different material than the distal portion 24 of the retrieval assembly.

The legs 21 of the proximal portion 22 of the retrieval assembly are made with rigid material, such as stainless steel, and are attached at their proximal end to an elongated member 40, and at their distal end 32 to the pocket edges 39 of the pocket in the distal portion 24 of the retrieval assembly. The legs 21 at their distal end 32 are attached to the pocket edges 39 by sutures, adhesives, loops, hooks or any other joining means known to a skilled person.

The pocket-shaped distal portion 24 of the retrieval assembly 15 is a netting or mesh made with a flexible material such as Nitinol. The openings in the mesh are large enough to permit fluids to pass but small enough to impede movement of material, such as stones larger than 0.1 mm, through the mesh.

The mesh of the distal portion 24 of the retrieval assembly 15 forms a pocket. In one embodiment, the apex 38 of the pocket in the distal portion 24 is positioned at the distal end 23 of the retrieval assembly 15. In this embodiment, the retrieval assembly is used to "net" or "sweep" material in a body tract. As illustrated in FIGS. 20A-20C, the retrieval device 10 is inserted into a body tract with the retrieval assembly 15 collapsed within the sheath 17 as illustrated in FIG. 20A. When the distal end 18 of the sheath 17 is advanced past a stone 60 or other material to be removed, the retrieval assembly 15 is extended beyond the distal end of the sheath as illustrated in FIG. 20B. With the retrieval assembly 15 positioned beyond the distal end of the sheath, the retrieval assembly 15 is manipulated around the stone 60 to capture the stone 60 in the pocket formed in the distal portion 24 of the retrieval assembly as illustrated in FIG. 20C.

In another embodiment of this aspect of the invention, illustrated in FIGS. 21A-21C, the apex 38 of the pocket in the distal portion 24 of the retrieval assembly 15 is located proximal to the ends 32 of the legs 21 of the proximal portion 22 of the retrieval assembly 15. In this embodiment, the pocket of the distal portion 24 of the retrieval assembly is used to "scoop" stones or other material in the body tract. The medical retrieval device is inserted into a body tract with the retrieval assembly 15 collapsed within the sheath 17 as illustrated in FIG. 21A. When the distal end 18 of the sheath 17 approaches the stone 60 or other material to be removed, the retrieval assembly 15 is moved to the position illustrated in FIG. 21B. With the retrieval assembly positioned as shown in FIG. 21B, the retrieval assembly 15 is advanced over the stone 60 capturing the stone 60 in the pocket of the distal portion 24 of the retrieval assembly 15 as illustrated in FIG. 21C.

Figure 22B:
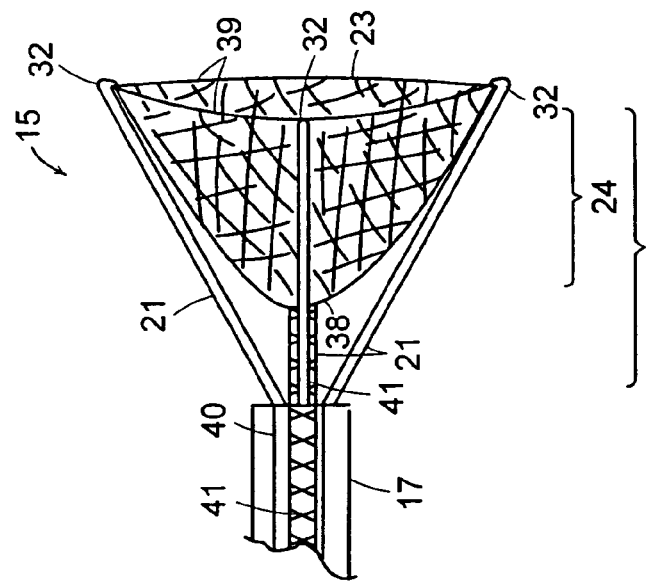
FIG. 22B illustrates another embodiment of the retrieval assembly illustrated in FIB. 19B.
Figure 22A:
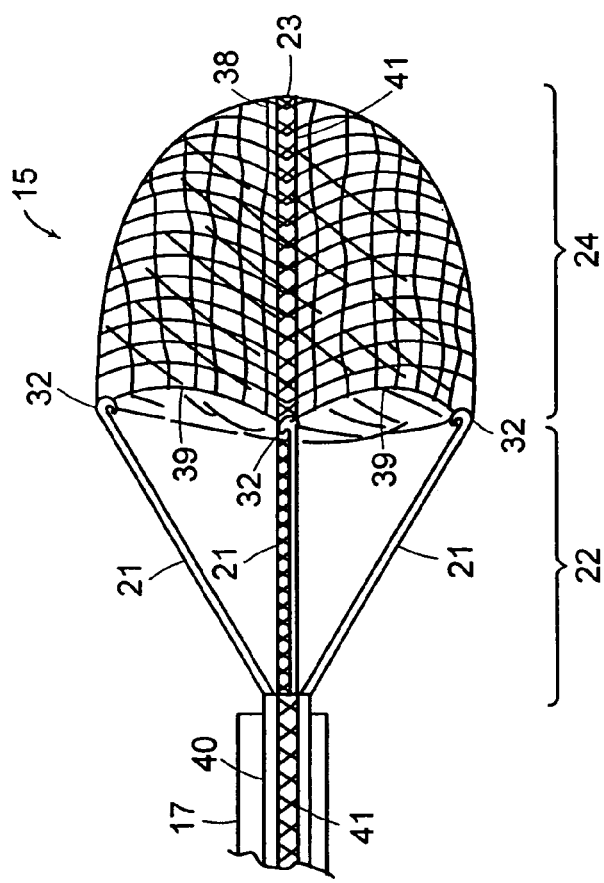
FIG. 22A illustrates another embodiment of the retrieval assembly illustrated in FIG. 19A.

Another embodiment of the invention illustrated in FIGS. 19A-19B, 20A-20C, and 21A-21C, is illustrated in FIGS. 22A and 22B. In this embodiment a second elongated guidewire 41 parallels or passes through an axially disposed lumen of guidewire 40 (see FIGS. 18D-18G for comparison) and is attached distally to the mesh of the distal end portion 24 of the retrieval assembly 15. The proximal end of second guidewire 41 is operatively joined at its proximal end to second actuator 42 in the manner illustrated in FIG. 18D. Axial movement of the guidewire 41 proximally causes retrieval assembly 15 to move from the everted position illustrated in FIG. 22A to the inverted position illustrated in FIG. 22B. Thus, with a first actuator 14 operatively attached to guidewire 40, and a second actuator 42 operatively attached to guidewire 41, the medical retrieval assembly 15 of the retrieval device 10 illustrated in FIGS. 19A-19B, 20A-20C, 21A-21C can be maneuvered to capture material in a body tract as illustrated in FIGS. 18E-18G and discussed in the corresponding text.

In general, the medical retrieval device according to the invention can be used in a clinical application to retrieve biological or foreign material from within a body. For example, the device can be used to retrieve a stone (e.g., a stone in the gall bladder, biliary tree, ureter, kidney, urinary bladder, urethra, etc.). The device could also be used to capture a thrombus or embolus within a vessel such as the coronary vessels of the heart or within the pulmonary vasculature. Regardless of the material being retrieved, the device 10 with the retrieval assembly 15 enclosed within a sheath 17 is inserted into a body tract. As the distal end 18 of the sheath approaches a stone 60, or passes to one side of a stone 60, the retrieval assembly is moved relative to the sheath 17 and extended beyond the distal end 15 of sheath 17. The retrieval assembly 15 is maneuvered around the stone 60 to capture the stone 60 within the confines of the retrieval assembly 15 after the stone 60 passes through the gap between the legs 21 of the retrieval assembly 15. The stone 60 may be approached from the side or from the proximal or distal end of the retrieval assembly. The stone 60 is captured in the retrieval assembly 15. The stone 60 is removed from the body tract by withdrawing the entire medical instrument 10 with the retrieval assembly 15 containing the stone 60, from the body tract.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A medical instrument, comprising:
a proximal handle;
a sheath extending from the handle and including a lumen, the sheath including a distal end away from the handle;
a retrieval assembly that is movable relative to the sheath to achieve a collapsed position of the retrieval assembly within the lumen and an expanded position of the retrieval assembly outside the lumen, the retrieval assembly including a proximal portion comprising three or more strands having a first rigidity and a distal portion comprising at least one wire having a second rigidity, wherein the three or more strands meet at a proximal-most end of the retrieval assembly, wherein the at least one wire is a single continuous wire that extends from a distal end of one of the strands to a distal end of another one of the strands, and wherein the distal portion of the retrieval assembly forms a pocket and includes an apex positioned at a distal end of the retrieval assembly; and
an elongate member having at least a portion formed of extensions of the three or more strands that are braided together, the elongate member extending proximally from the proximal-most end of the retrieval assembly.

2. The medical instrument of claim 1, wherein the proximal portion of the retrieval assembly comprises a first material and the distal portion of the retrieval assembly comprises a second material different from the first material.

3. The medical instrument of claim 2, wherein the second material is more flexible than the first material.

4. The medical instrument of claim 1, wherein axial movement of the elongate member in a proximal direction collapses the distal portion of the retrieval assembly.

5. The medical instrument of claim 1, wherein moving the sheath in a distal direction causes the retrieval assembly to collapse when it enters the lumen.

6. The medical instrument of claim 1, wherein at least one strand of the three or more strands comprises twisted or braided wire.

7. The medical instrument of claim 1, wherein the at least one wire continues to extend back from the distal end of the another strand to the distal end of the one strand to form a first wire and a second wire disposed adjacent to one another.

8. The medical instrument of claim 7, wherein a distal end of the first wire does not pass through a loop formed by the second wire.

9. The medical instrument of claim 7, wherein a distal end of the first wire is not interlocked with the second wire.

10. The medical instrument of claim 1, wherein the proximal portion and the distal portion are discrete parts comprising different materials and coupled together using joints.

11. The medical instrument of claim 10, wherein at least one of the joints includes one of a crimp, a hole, a loop, a hook, a solder, a weld, a knot, and an adhesive.

12. A medical instrument, comprising:
a proximal handle;
a sheath extending from the handle and including a lumen, the sheath including a distal end away from the handle;
a retrieval assembly that is movable relative to the sheath to achieve a collapsed position of the retrieval assembly within the lumen and an expanded position of the retrieval assembly outside the lumen, the retrieval assembly including a proximal portion comprising a plurality of strands, and a distal portion comprising a plurality of filaments, each of the plurality of strands being discrete from each of the plurality of filaments, and a distal end of at least one of the strands being connected to a proximal end of at least one of the filaments by a joint, the joint including at least one of a crimp, a hole, a loop, a hook, a solder, a weld, a knot, and an adhesive;
wherein the at least one filament is a single continuous wire that extends from the distal end of one of the strands to the distal end of another one of the strands, wherein the distal portion of the retrieval assembly forms a pocket and includes an apex positioned at a distal end of the retrieval assembly; and
an elongate member having at least a portion formed of extensions of the plurality of strands that are braided together.

13. The medical instrument of claim 12, wherein axial movement of the elongate member in a proximal direction collapses the distal portion of the retrieval assembly.

14. The medical instrument of claim 12, wherein a strand of the plurality of strands is made of a first material having a first rigidity and a filament of the plurality of filaments is made of a second material having a second rigidity different from the first rigidity.

15. The medical instrument of claim 14, wherein the second material is more flexible than the first material.

16. The medical instrument of claim 12, wherein the plurality of strands include at least three strands that are not coplanar when the retrieval assembly is outside the lumen.

17. The medical instrument of claim 12, wherein the plurality of filaments include at least two filaments that extend from the distal end of the one strand to the distal end of the another strand.

18. A medical instrument, comprising:
a proximal handle;
a sheath extending from the handle and including a lumen, the sheath including a distal end away from the handle;
a retrieval assembly that is movable relative to the sheath to achieve a collapsed position of the retrieval assembly within the lumen and an expanded position of the retrieval assembly outside the lumen, the retrieval assembly comprising a distal portion and a proximal portion, the proximal portion and the distal portion being discrete parts coupled together by joints, the proximal portion including three or more legs including a first material and the distal portion includes at least one single continuous wire including a second material different from the first material, the at least one single continuous wire extending between distal ends of a first leg and a second leg of the three or more legs, the at least one single continuous wire being coupled to the distal ends of the first leg and the second leg by joints, and wherein the distal portion of the retrieval assembly forms a pocket and includes an apex positioned at a distal end of the retrieval assembly; and
an elongate member having at least a portion formed of extensions of the three or more legs that are braided together.

19. The medical instrument of claim 18, wherein the second material is more flexible than the first material.

20. The medical instrument of claim 18, wherein the second material is selected from a group consisting of nitinol, silk, nylon, nickel-titanium, nickel-titanium-copper, and nickel-titanium-lead.

21. The medical instrument of claim 18, wherein the at least one single continuous wire includes a first wire that extends from the distal end of the first leg to the distal end of the second leg and a second wire that extends from the distal end of the second leg to the distal end of the first leg, the first wire and the second wire being a single continuous wire.

22. The medical instrument of claim 18, wherein the retrieval assembly is movable relative to the sheath to achieve another position of the retrieval assembly in which at least a portion of the retrieval assembly extends from the distal end of the sheath and assumes a three-dimensional shape out of the lumen of the sheath.

23. The medical instrument of claim 18, wherein the elongate member extends within the lumen from the handle to the retrieval assembly.

24. The medical instrument of claim 18, wherein one of the joints between the proximal portion and the distal portion includes one of a crimp, a hole, a loop, a hook, a solder, a weld, a knot, or an adhesive.

25. A medical instrument, comprising:
a proximal handle;
a sheath extending from the handle and including a lumen, the sheath including a distal end away from the handle;
a retrieval assembly that is movable relative to the sheath to achieve a collapsed position of the retrieval assembly within the lumen and an expanded position of the retrieval assembly outside the lumen, the retrieval assembly comprising a proximal portion having a plurality of legs that meet at a proximal-most end of the retrieval assembly and a distal portion comprising a plurality of wires, wherein the plurality of wires include a first wire that is a single continuous wire that extends from a distal end of a first leg of the plurality of legs to a distal end of a second leg of the plurality of legs and continues back from the distal end of the second leg to the distal end of the first leg, wherein joints connect the first wire to the distal ends of the first leg and the second leg, and wherein the distal portion of the retrieval assembly forms a pocket and includes an apex positioned at a distal end of the retrieval assembly; and
an elongate member having at least a portion formed of extensions of the plurality of legs that are braided together, the elongate member extending proximally from the proximal-most end of the retrieval assembly.

26. The medical instrument of claim 25, wherein at least one of the joints comprises a loop positioned at a distal end of a leg of the plurality of legs.

27. The medical instrument of claim 25, wherein at least one of the joints comprises a hook positioned at a distal end of a leg of the plurality of legs.

28. The medical instrument of claim 25, wherein at least one of the joints comprises a crimp.

29. The medical instrument of claim 25, wherein each of the plurality of legs comprises a first material and the first wire comprises a second material, the second material being different from, and more flexible than, the first material.

30. The medical instrument of claim 25, wherein the plurality of legs include at least three legs that are non coplanar when the retrieval assembly is in the expanded configuration.

31. A medical instrument, comprising:
a proximal handle;
a sheath extending from the handle and including a lumen, the sheath including a distal end away from the handle; and
a retrieval assembly that is movable relative to the sheath to achieve a collapsed position of the retrieval assembly within the lumen and an expanded position of the retrieval assembly outside the lumen, the retrieval assembly including a proximal portion comprising three or more strands of a first material and a distal portion comprising at least a first wire of a second material which is more flexible than the first material, the first wire being discrete from the strands and coupled at one end to a distal end of a first strand of the three or more strands and at an opposite end to the distal end of a second strand of the three or more strands, wherein the three or more strands meet at a proximal-most end of the retrieval assembly and are braided together to form an elongate section that extends proximally from the proximal-most end, and wherein the distal portion of the retrieval assembly forms a pocket and includes an apex positioned at a distal end of the retrieval assembly.

32. The medical instrument of claim 31, further including a second wire disposed adjacent to the first wire and extending between the first strand and the second strand, the first wire and the second wire being a single continuous wire.

33. The medical instrument of claim 31, wherein the proximal portion and the distal portion of the retrieval assembly are discrete parts that are coupled together using joints, the joints including at least one of a crimp, a hole, a loop, a hook, a solder, a weld, a knot, and an adhesive.

34. A medical instrument, comprising:
a proximal handle;
a sheath extending from the handle and including a lumen, the sheath including a distal end away from the handle; and
a retrieval assembly that is movable relative to the sheath to achieve a collapsed position of the retrieval assembly within the lumen and an expanded position of the retrieval assembly outside the lumen, the retrieval assembly including a proximal portion comprising three or more strands and a distal portion comprising a first single continuous wire which is discrete from, and more flexible than, the three or more strands, the first wire being connected at one end to a distal end of one of the strands and at an opposite end to the distal end of another one of the strands, and a second single continuous wire, which is discrete from the three or more strands and the first wire, extending from a distal end of one strand to a distal end of another strand, wherein a distal end of the first wire does not pass through a loop formed by the second wire.

35. The medical instrument of claim 34, wherein joints connect the first wire to the distal ends of two strands of the three or more strands, at least one of the joints including one of a crimp, a hole, a loop, a hook, a solder, a weld, a knot, and an adhesive.

36. A medical instrument, comprising:
a proximal handle;
a sheath extending from the handle and including a lumen, the sheath including a distal end away from the handle; and
a retrieval assembly that is movable relative to the sheath to achieve a collapsed position of the retrieval assembly within the lumen and an expanded position of the retrieval assembly outside the lumen, the retrieval assembly comprising:

a proximal portion including a plurality of strands, wherein the plurality of strands meet at a proximal-most end of the retrieval assembly and are braided together to form an elongate section that extends proximally from the proximal-most end; and a distal portion including at least two single continuous wires that are discrete from the plurality of strands, wherein each of the at least two single continuous wires extends from a distal end of one of the strands to a distal end of another one of the strands, and neither of the at least two single continuous wires pass through a loop formed by the other of the at least two single continuous wires.

37. The medical instrument of claim 36, wherein the plurality of strands include at least three strands made of a first material which is less flexible than a material of the at least two single continuous wires in the distal portion.

38. The medical instrument of claim 36, wherein the proximal portion and the distal portion of the retrieval assembly are discrete parts that are coupled together using joints, at least one of the joints including one of a crimp, a hole, a loop, a hook, a solder, a weld, a knot, and an adhesive.

\* \* \* \* \*

UNITED STATES PATENT AND TRADEMARK OFFICE
CERTIFICATE OF CORRECTION

| | | |
|---|---|---|
| PATENT NO. | : 8,828,022 B2 | Page 1 of 1 |
| APPLICATION NO. | : 11/030044 | |
| DATED | : September 9, 2014 | |
| INVENTOR(S) | : White et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1297 days.

Signed and Sealed this
Twenty-ninth Day of September, 2015

Michelle K. Lee
*Director of the United States Patent and Trademark Office*